US007728965B2

(12) United States Patent
Haller et al.

(10) Patent No.: US 7,728,965 B2
(45) Date of Patent: Jun. 1, 2010

(54) SYSTEMS AND METHODS FOR INSPECTING AN EDGE OF A SPECIMEN

(75) Inventors: Kurt Lindsay Haller, Pleasanton, CA (US); Steve Yifeng Cui, Fremont, CA (US); Jared Lera, San Jose, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 377 days.

(21) Appl. No.: 11/145,874

(22) Filed: Jun. 6, 2005

(65) Prior Publication Data

US 2006/0274304 A1 Dec. 7, 2006

(51) Int. Cl.
*G01N 21/00* (2006.01)
(52) U.S. Cl. ............................................. 356/237.1
(58) Field of Classification Search .... 356/237.1–237.6
See application file for complete search history.

(56) References Cited

U.S. PATENT DOCUMENTS

| | | | |
|---|---|---|---|
| 6,201,601 B1 | 3/2001 | Vaez-Iravani et al. | |
| 6,271,916 B1 | 8/2001 | Marxer et al. | |
| 6,538,730 B2 | 3/2003 | Vaez-Iravani et al. | |
| 6,590,645 B1 * | 7/2003 | Chen et al. | 356/237.2 |
| 7,130,036 B1 * | 10/2006 | Kuhlmann et al. | 356/237.2 |
| 7,130,039 B2 * | 10/2006 | Vaez-Iravani et al. | 356/237.5 |
| 7,161,667 B2 | 1/2007 | Meeks et al. | |
| 7,161,668 B2 | 1/2007 | Meeks et al. | |
| 7,161,669 B2 | 1/2007 | Velidandla et al. | |
| 7,280,197 B1 * | 10/2007 | Rosengaus | 356/237.1 |
| 7,280,200 B2 | 10/2007 | Plemmons et al. | |
| 2002/0122174 A1 * | 9/2002 | Hamamatsu et al. | 356/237.2 |
| 2003/0030050 A1 | 2/2003 | Choi | |
| 2003/0030795 A1 | 2/2003 | Swan et al. | |
| 2003/0067598 A1 * | 4/2003 | Tomie | 356/237.2 |
| 2003/0169916 A1 * | 9/2003 | Hayashi et al. | 382/145 |
| 2003/0210393 A1 * | 11/2003 | Vaez-Iravani et al. | 356/237.4 |
| 2004/0085532 A1 * | 5/2004 | Chen et al. | 356/237.2 |
| 2004/0169852 A1 * | 9/2004 | Chen et al. | 356/237.2 |
| 2005/0002023 A1 * | 1/2005 | Kreh et al. | 356/237.5 |
| 2005/0013474 A1 * | 1/2005 | Sim | 382/145 |
| 2005/0036671 A1 * | 2/2005 | Watkins et al. | 382/145 |
| 2005/0094136 A1 * | 5/2005 | Xu et al. | 356/237.3 |

* cited by examiner

*Primary Examiner*—Tarifur R. Chowdhury
*Assistant Examiner*—Isiaka O Akanbi
(74) *Attorney, Agent, or Firm*—Ann Marie Mewherter

(57) ABSTRACT

Systems and methods for inspecting an edge of a specimen are provided. One system includes an illumination subsystem configured to direct light to the edge of the specimen at an oblique angle of incidence. The plane of incidence of the light is substantially perpendicular to a plane substantially tangent to the edge of the specimen. The system also includes a detection subsystem configured to collect light scattered from the edge and to generate signals responsive to the scattered light. One method includes directing light to the edge of the specimen at an oblique angle of incidence. The plane of incidence is substantially perpendicular to a plane substantially tangent to the edge of the specimen. The method also includes collecting light scattered from the edge and generating signals responsive to the scattered light. The signals described above can be used to detect defects on the edge of the specimen.

20 Claims, 4 Drawing Sheets

SYSTEMS AND METHODS FOR INSPECTING AN EDGE OF A SPECIMEN

BACKGROUND OF THE INVENTION

1. Field of the Invention

The present invention generally relates to systems and methods for inspecting an edge of a specimen. Certain embodiments relate to a system that includes an illumination subsystem that is configured to direct light to the edge of the specimen at an oblique angle of incidence.

2. Description of the Related Art

The following description and examples are not admitted to be prior art by virtue of their inclusion in this section.

Fabricating semiconductor devices such as logic and memory devices typically includes processing a specimen such as a semiconductor wafer using a number of semiconductor fabrication processes to form various features and multiple levels of the semiconductor devices. For example, lithography is a semiconductor fabrication process that typically involves transferring a pattern to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a semiconductor wafer and then separated into individual semiconductor devices.

Wafers may contain defects both in central regions of the wafers as well as in edge regions, which include a relatively narrow region around the periphery of the wafers, and the edges of the wafers. Examples of defects that may be found in the edge region and on the edge of wafers include, but are not limited to, chips, cracks, scratches, marks, particles, and residual chemicals (e.g., resist and slurry). As wafer sizes continue to increase, both wafer and integrated circuit (IC) manufacturers are becoming more concerned about defectivity at or near the wafer edge. The main concerns are that edge defects could fall onto the central part of the wafer thereby causing untraceable yield loss, cross contamination during processing, and/or catastrophic wafer breakage. These yield loss mechanisms are experienced by most wafer and IC manufacturers at one time or another.

Traditionally, wafer inspection tools are designed to inspect a central region of the wafers (i.e., a surface of the wafer on which electrical elements will be formed or a surface of the wafer opposite that on which electrical elements will be formed). Since these areas of the wafer reflect or scatter relatively small amounts of light, such wafer inspection tools are designed to detect relatively small amounts of light. However, near the edge of the wafer, relatively large amounts of light may be reflected or scattered from the wafer due to edge features such as a bevel formed in the edge. As a result, these large amounts of light will saturate the detectors of traditional wafer inspection systems. Consequently, any output signals generated near or at the edge of wafers by such wafer inspection tools are generally unusable. In some instances, the wafer inspection systems may be designed to block light from reaching the detectors when inspecting near the edge of the wafer to protect the detectors from damage that may be caused by the relatively high intensity light.

Edge inspection of specimens may be currently performed manually by visual (unaided human eye) inspection with incoherent light sources or by visual inspection aided by manual or automated wafer-handling light microscopy. However, some edge inspection systems have been developed to detect defects at or near the edge of wafers. Some edge inspection systems use digital microscopic image acquisition with a plurality of imaging devices and incoherent or coherent illumination to image different edge regions of a semiconductor wafer with computer processing of the images by a defect detection and classification algorithm. Additional examples of apparatuses for detecting defects along the edge of electronic media such as semiconductor wafers are illustrated in U.S. Patent Application Publication Nos. 2003/0030050 by Choi and 2003/0030795 by Swan et al., which are incorporated by reference as if fully set forth herein.

Due to the substantially different reflecting and scattering characteristics of the edge of wafers in comparison to the central region of the wafer, such edge inspection systems have substantially different configurations than traditional wafer inspection tools. Therefore, the edge inspection systems are not optimized to, or even able to, detect defects in the central region of the wafers. Consequently, if wafer or IC manufacturers want to detect defects in both the central and outer regions of wafer (as is usually the case since defects in either region may result in expensive yield losses and other problems), they will need to purchase two separate tools. For example, edge inspection may be performed using an additional stand alone inspection tool or an additional subsystem on an existing inspection tool.

Using two different wafer inspection tools instead of just one inspection tool will obviously increase costs in many ways such as increases in clean room real estate costs, operating costs, tool maintenance costs, and reduced throughput. However, since most inspection tools are not capable of inspecting both the inner region and edge of wafers, and due to the increasing costs associated with defect-based yield losses, wafer and IC manufacturers may not be able to avoid the costs associated with multiple, different inspection tools. In addition, incorporating an additional subsystem into an existing inspection tool will also increase the overall cost of the tool due to the hardware and possibly software required for the additional inspection subsystem and increased maintenance costs for the additional subsystem.

Accordingly, it may be advantageous to develop systems and methods for inspecting an edge of a specimen that are capable of inspecting the entire edge of the specimen, including the top bevel, the apex, and the bottom bevel, and can be implemented on an existing inspection system with relatively inexpensive changes to the configuration of the existing inspection system.

SUMMARY OF THE INVENTION

The following description of various embodiments of systems and methods for inspecting an edge of a specimen is not to be construed in any way as limiting the subject matter of the appended claims.

One embodiment relates to a system configured to inspect an edge of a specimen. The system includes an illumination subsystem that is configured to direct light to the edge of the specimen at an oblique angle of incidence. The plane of incidence of the light is substantially perpendicular to a plane that is substantially tangent to the edge of the specimen. The system also includes a detection subsystem that is configured to collect light scattered from the edge of the specimen and to generate signals responsive to the scattered light. The signals can be used to detect defects on the edge of the specimen.

In one embodiment, the edge of the specimen includes a top bevel, an apex, and a bottom bevel of the specimen. In some embodiments, the system is configured to scan the light across the edge of the specimen by rotating and translating the specimen substantially simultaneously. In another embodiment; the system is configured to scan the light across the edge of the specimen by scanning the light beyond a nominal edge of the specimen by a distance of about 2 mm to about 3 mm. In a further embodiment, the system is configured to scan the light across the edge of the specimen by scanning the light from a position on an upper surface of the specimen proximate the edge to a position beyond a nominal edge of the specimen.

In an embodiment, the detection subsystem includes a mask that is configured to substantially prevent light specularly reflected from the edge of the specimen from impinging upon a detector of the detection subsystem. In some embodiments, the system includes a processor that is configured to determine a position of the defects on the edge of the specimen using the signals. In some embodiments, patterned features are located on an upper surface of the specimen proximate to the edge of the specimen. In one such embodiment, the system includes a processor that is configured to determine which of the signals correspond to the light scattered from the patterned features and to eliminate the signals corresponding to the light scattered from the patterned features from the signals used to detect the defects.

In another embodiment, the system is also configured to inspect an upper surface of the specimen. In such an embodiment, parameters of the system used for inspection of the upper surface of the specimen are different than parameters of the system used for inspection of the edge of the specimen. In an additional embodiment, the system is configured to inspect a bottom surface of the specimen. In some embodiments, the specimen includes a patterned or unpatterned wafer. Each of the embodiments of the system described above may be further configured as described herein.

Another embodiment relates to a method for inspecting an edge of a specimen. The method includes directing light to the edge of the specimen at an oblique angle of incidence. The plane of incidence of the light is substantially perpendicular to a plane substantially tangent to the edge of the specimen. The method also includes collecting light scattered from the edge of the specimen. In addition, the method includes generating signals responsive to the scattered light. The signals can be used to detect defects on the edge of the specimen.

In one embodiment, the edge of the specimen includes a top bevel, an apex, and a bottom bevel of the specimen. In another embodiment, directing the light to the edge of the specimen includes scanning the light across the edge of the specimen by rotating and translating the specimen substantially simultaneously. In some embodiments, directing the light to the edge of the specimen includes scanning the light beyond a nominal edge of the specimen by a distance of about 2 mm to about 3 mm. In a further embodiment, directing the light to the edge of the specimen includes scanning the light across the specimen from a position on an upper surface of the specimen proximate the edge to a position beyond a nominal edge of the specimen.

In an embodiment, the method includes substantially preventing light specularly reflected from the edge of the specimen from impinging upon a detector used for generating the signals. In another embodiment, the method includes determining a position of the defects on the edge of the specimen using the signals. In some such embodiments, the position includes x and y coordinates of the position of the defects. In another embodiment, the edge of the specimen includes a top bevel, an apex, and a bottom bevel of the specimen. In such an embodiment, the method may include determining if the defects are located on the top bevel, the apex, or the bottom bevel using the signals.

In some embodiments, patterned features are located on an upper surface of the specimen proximate to the edge of the specimen. In one such embodiment, the method includes determining which of the signals correspond to the light scattered from the patterned features and eliminating the signals corresponding to the light scattered from the patterned features from the signals used to detect the defects.

In some embodiments, the method includes inspecting an upper surface of the specimen. In such an embodiment, parameters used for inspecting the upper surface of the specimen are different than parameters used for inspecting the edge of the specimen. In another embodiment, the method includes inspecting a bottom surface of the specimen. In an additional embodiment, the specimen includes a patterned or unpatterned wafer. Each of the embodiments of the method described above may include any other step(s) described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
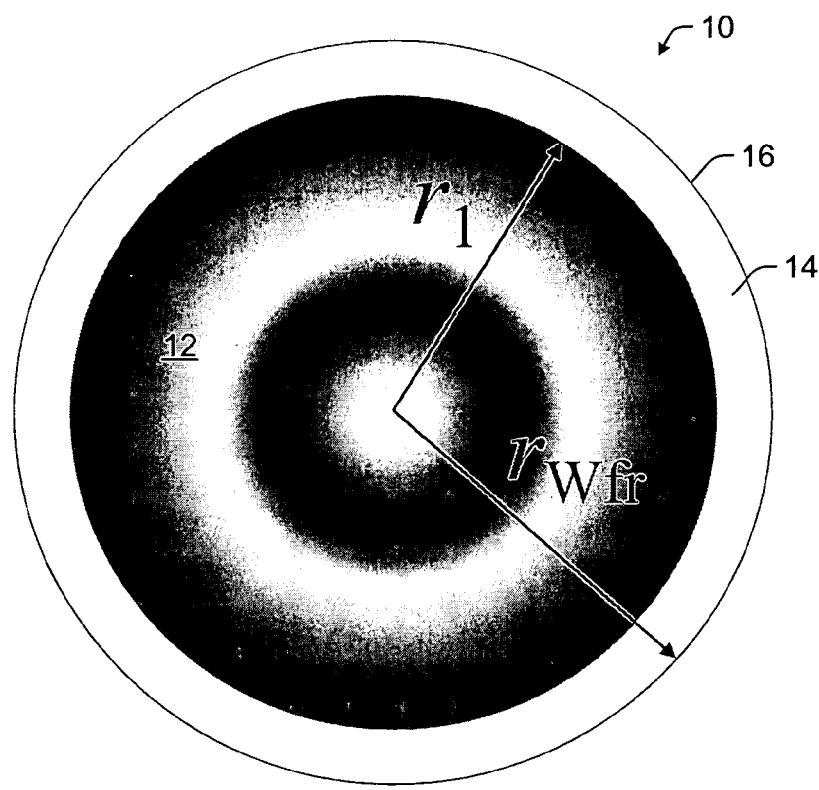
FIG. 1 is a schematic diagram illustrating a top view of a specimen such as a wafer.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "specimen" generally refers to a wafer or any other specimen having an edge on which defects of interest may be located. Although the terms "specimen" and "wafer" are used interchangeably herein, it is to be understood that embodiments described with respect to a wafer may configured and/or used for inspection of any other specimen as described above.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

One or more layers may be formed upon a wafer. For example, such layers may include, but are not limited to, a resist, a dielectric material, and a conductive material. Many different types of such layers are known in the art, and the term wafer as used herein is intended to encompass a wafer on which all types of such layers may be formed. One or more layers formed on a wafer may be patterned. For example, a wafer may include a plurality of dies, each having repeatable pattern features. Formation and processing of such layers of material may ultimately result in completed semiconductor devices. As such, a wafer may include a substrate on which not all layers of a complete semiconductor device have been formed or a substrate on which all layers of a complete semiconductor device have been formed.

The wafer may further include at least a portion of an integrated circuit, a thin-film head die, a micro-electro-mechanical system (MEMS) device, flat panel displays, magnetic heads, magnetic and optical storage media, other components that may include photonics and optoelectronic devices such as lasers, waveguides and other passive components processed on wafers, print heads, and bio-chip devices processed on wafers.

Turning now to the drawings, it is noted that FIGS. 1-6 are not drawn to scale. In particular, the scale of some of the elements of the figures is greatly exaggerated to emphasize characteristics of the elements. It is also noted that FIGS. 1-6 are not drawn to the same scale. Elements shown in more than one figure that may be similarly configured have been indicated using the same reference numerals.

FIG. 1 illustrates a top view of wafer 10. As shown in FIG. 1, wafer 10 includes center region 12 having a radius $r_1$ and edge region 14. Edge region 14 is located adjacent to the periphery of the surface of the wafer defined by nominal edge 16 and completely surrounds the center region of the wafer. In some embodiments, edge region 14 extends about 3 mm inward from nominal edge 16 of the wafer. However, the edge region may extend more than about 3 mm inward from the nominal edge of the wafer (e.g., about 5 mm or about 6 mm). The extent of the edge region may vary depending upon, for example, the size of the wafer, the characteristics of the semiconductor devices or integrated circuits being formed upon the wafer, and parameters of the semiconductor fabrication process used to process the wafer.

Edge region 14 and center region 12 have a combined radius of $r_{wfr}$. In other words, the center region and the edge region have a combined surface area approximately equal to an entire surface area of an upper surface or a bottom surface of the wafer. The upper surface of the wafer is defined as the surface of the wafer on which patterned features will be formed during fabrication of semiconductor devices or other components on the wafer. In some instances, the patterned features will be formed only in center region 12. However, the patterned features may be formed in center region 12 and edge region 14. The bottom surface of the wafer is defined as the surface of the wafer on which such patterned features will generally not be formed during fabrication.

Figure 2:
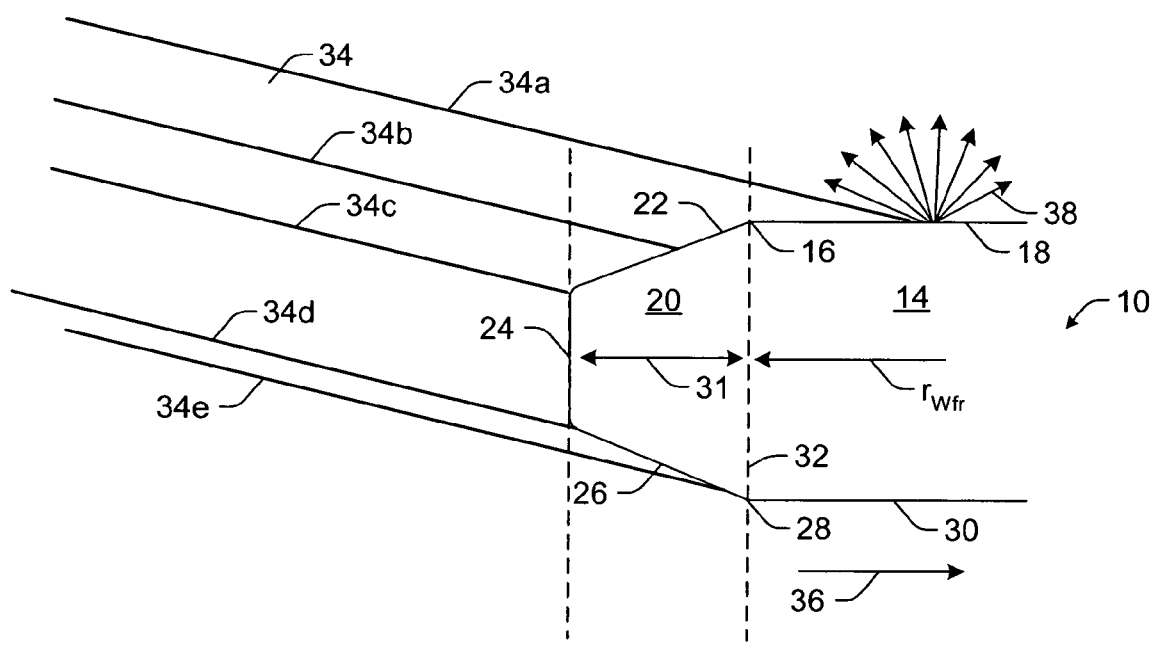
FIG. 2 is a schematic diagram illustrating a partial cross-sectional view of a specimen and light directed to an edge of the specimen at an oblique angle of incidence according to an embodiment.

As shown in FIG. 2, which is a partial cross-sectional view of wafer 10, upper surface 18 of the wafer extends to nominal edge 16 of the wafer. Therefore, the portion of the upper surface of the wafer shown in FIG. 2 is located in edge region 14 described above. Edge 20 of the wafer includes top bevel 22, apex 24, and bottom bevel 26. Top bevel 22 extends from nominal edge 16 of the wafer to apex 24. As further shown in FIG. 2, a surface of top bevel 22 is arranged at an angle with respect to upper surface 18 and apex 24 of the wafer. Bottom bevel 26 extends from apex 24 to nominal edge 28 of bottom surface 30 of the wafer. The portion of bottom surface 30 shown in FIG. 2 constitutes a portion of the edge region of the bottom surface as described above. As further shown in FIG. 2, a surface of bottom bevel 26 is arranged at an angle with respect to apex 24 and bottom surface 30. Edge 20 of the wafer may have lateral dimension 31 extending from apex 22 to plane 32, which extends through nominal edges 16 and 26, of about 0.5 mm. The lateral dimension of the edge may vary depending upon, for example, the size of the wafer.

Defects in the center region of the wafer have been the primary concern for wafer and integrated circuit (IC) manufacturers since this is the area of the wafer upon which IC and semiconductor devices are fabricated. Therefore, many wafer inspection systems have been designed to detect defects in the center portion of the wafer. However, as described in more detail above, wafer and IC manufacturers are becoming more concerned about defects at or near the wafer edge. Since many traditional wafer inspection tools are not capable of inspecting wafers at or near the wafer edge, some wafer inspection systems have been developed for inspection of areas at or near the wafer edge. Such wafer edge inspection tools, however, are not capable of inspecting the center region of wafers due to the configuration of these tools. As such, a wafer inspection tool that can inspect both the center region and edge of a wafer may be particularly advantageous for reducing inspection costs and increasing throughput for inspection and thereby for wafer and IC manufacturing.

Various systems and methods for inspecting an edge of a specimen such as a wafer are described herein. The systems and methods described herein are advantageous for many reasons. For example, the systems and methods described herein can be used to inspect both the center region and edge of a wafer. Therefore, edge inspection and upper and/or bottom surface inspection can be performed by a single system or method. The parameters of the system or method can be changed between edge inspection and inspection of an upper and/or bottom surface of a wafer. For instance, one or more parameters of the system or method that may be altered between edge and upper or bottom surface inspection may include, but are not limited to, positioning a mask in the system as described herein depending on which inspection is to be performed. Therefore, the systems and methods described herein can perform edge inspection of a specimen using an existing system configuration having one or more modified parameters. In this manner, the systems and methods described herein may reduce the number of tools required to inspect an entire surface of a wafer, including the edge and upper and/or bottom surfaces, thereby reducing wafer and IC manufacturers' capital and operating costs. In addition, since the entire wafer surface can be inspected in one system, wafer inspection throughput can be increased thereby increasing the overall manufacturing throughput.

Preferably, for edge inspection of a wafer, light 34 is directed to edge 20 of the wafer at an oblique angle of incidence, as shown in FIG. 2. In addition, the plane of incidence of light 34 is preferably substantially perpendicular to a plane that is substantially tangent to the edge of the specimen. In particular, the plane of incidence is preferably substantially perpendicular at all times to a plane tangent to the curve (often a compound curve) of the wafer edge bevel and apex surfaces at the point the light impinges on these surfaces.

Such an arrangement between the light and the edge of the wafer advantageously increases the area of the edge of the wafer that can be inspected. For example, as shown in FIG. 2, light 34 can illuminate the edge of the wafer down to the bottom of apex 24. Therefore, such illumination is advantageous since even relatively small defects and partially subsurface defects on the top bevel and apex will receive adequate illumination. Therefore, the light scattered from these and other defects on the edge of the specimen will produce relatively strong light scattering when illuminated as shown in FIG. 2. In contrast, if normal incidence is used for edge inspection, defects that do not "stick out" or extend beyond the nominal wafer edge may produce relatively weal light scattering.

Similar problems in the light scattering levels of edge defects will be evident when using light that is directed to the edge of a wafer at an oblique angle of incidence in a plane of incidence that is substantially parallel to a plane substantially tangent to the curve of the bevel and apex surfaces. Such a plane of incidence is increasingly being used in systems that scan oblique incidence light in a spiral path over a surface of a wafer to reduce the light that is reflected or scattered from the edge of the wafer. In this manner, such a plane of incidence provides relatively high sensitivity scans with relatively small edge exclusion. However, due to the plane of incidence specifically selected for such systems, these systems will be particularly unsuitable for edge inspection without major redesign of the optics.

As shown in FIG. 2, light 34 may scan across upper surface 18 of wafer 10 then across top bevel 22 and apex 24. Such scanning is illustrated in FIG. 2 by different light beams that illustrate the different positions of light 34 during scanning. In particular, in the direction of scanning, light 34 may be directed first to upper surface 18 as indicated by the position of light beam 34a. Light 34 may be scanned over upper surface 18 and then over top bevel 22 and apex 24 as indicated by the different positions of light beam 34b, light beam 34c, and light beam 34d.

As further shown in FIG. 2, light 34 may be scanned over the edge of the wafer to a position beyond the bottom of the apex. For instance, light 34 may be scanned from the bottom of apex 24 as indicated by the position of light beam 34d across bottom bevel 26 as indicated by the position of light beam 34e. In this manner, light 34 may be scanned over the bottom bevel on the edge of the specimen such that defects can be detected on the bottom bevel. Although the plane of incidence may not be substantially perpendicular to a plane substantially tangent to the surface of the bottom bevel, such illumination may be sufficient for detection of the defects of interest on the bottom bevel. In addition, the specimen may be "flipped over" as described further herein such that the positions of the top and bottom bevels shown in FIG. 2 may be switched. The specimen may be flipped over for inspection of the bottom surface of the specimen. In this manner, the bottom bevel inspection may be performed before or after inspection of the bottom surface while the specimen is in this flipped position.

The light may be scanned over the portion of the upper surface and edge of the wafer as described further herein. For example, the position of light 34 may be stationary while wafer 10 is moved in a direction shown by arrow 36. The wafer may be moved in this direction during inspection as described further herein. However, in other embodiments, the wafer may be stationary, and the light may be moved in a direction opposite to that shown by arrow 36. In addition, the wafer and the light may be moved in substantially opposite directions to cause scanning of the wafer.

As further shown in FIG. 2, light 38 may be scattered from upper surface 18 of wafer 10 as a result of illumination. Light (not shown) may also be scattered from the edge of the wafer as a result of the illumination. As shown in FIG. 2, the light may be scattered from the upper surface in a number of non-specular directions. The exact directions in which light will be scattered vary depending on the characteristics of the light used for illumination and the characteristics of the portion of the specimen on which the light is incident. In addition, characteristics of the scattered light other than or in addition to the scattering direction (e.g., polarization, intensity, etc.) may vary due to characteristics of the light and the specimen. Therefore, the light that is scattered from the specimen as a result of the oblique illumination shown in FIG. 2 may be used to determine characteristics of the specimen. In particular, as described further herein, the scattered light may be collected and signals responsive to the scattered light can be used to detect defects on the edge of the specimen. Such signals may also be used to detect defects on an upper and/or bottom surface of the specimen.

Figure 3:
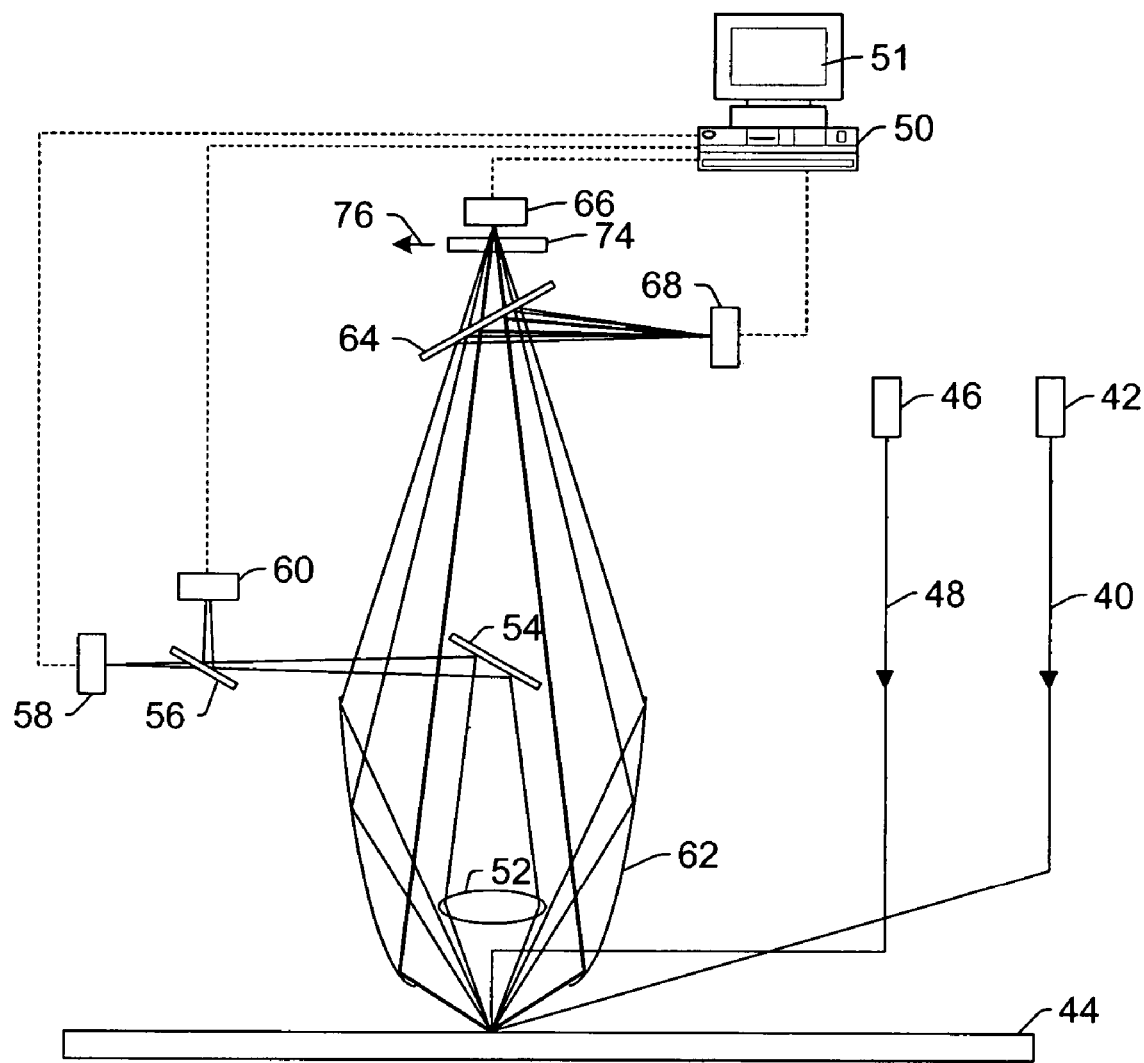
FIG. 3 is a schematic diagram illustrating a cross-sectional view of one embodiment of a system that can be configured to inspect an edge of a specimen as described herein.

One embodiment of a system that is configured to inspect an edge of a specimen is illustrated in FIG. 3. The system shown in FIG. 3 is configured for unpatterned wafer inspection and is based on the SP1$^{TBI}$ system, which is commercially available from KLA-Tencor, San Jose, Calif., with modifications described herein. This inspection system is described in more detail in U.S. Pat. No. 6,538,730 to Vaez-Iravani et al., which is incorporated by reference as if fully set forth herein. The system shown in FIG. 3 may further be configured as described in this patent for patterned and unpatterned wafer inspection. For the sake of clarity, some of the components and details of the system have been omitted from FIG. 3 and the corresponding description presented herein. In addition, U.S. Pat. No. 6,538,730 is related to U.S. Pat. No. 6,201,601 to Vaez-Iravani et al. and U.S. Pat. No. 6,271,916 to Marxer et al., which are also incorporated by reference as if fully set forth herein. The system shown in FIG. 3 may be further configured as described in these patents.

The system shown in FIG. 3 includes an illumination subsystem. The illumination subsystem may be configured to generate light 40. For instance, the illumination subsystem may include light source 42, which is configured to generate light 40. The illumination subsystem is configured to direct light 40 to the edge (not shown in FIG. 3) of wafer 44 at an oblique angle of incidence as described above. For example, the illumination subsystem may include a number of optical components (not shown) positioned in a path of light 40 such that the light can be directed to the edge of the wafer at a suitable oblique angle of incidence. The optical components positioned in the path of light 40 may include, for example, folding mirror(s), beam splitter(s), and lenses. The angle of incidence may vary depending on, for example, the characteristics of the light and the characteristics of the edge of the specimen. One suitable angle of incidence may be about 70° from normal to the upper surface of the wafer. The plane of incidence of light 40 is preferably substantially perpendicular to a plane substantially tangent to the edge of the specimen as described above. The illumination subsystem may also include a number of other optical components (not shown) positioned in the path of light 40 such as polarizing component(s) and filter(s).

The illumination subsystem may, in some embodiments, include light source 46. Light source 46 is configured to generate light 48, which is directed by the illumination subsystem to wafer 44 at a substantially normal angle of incidence. Light 48 may or may not be directed to the edge of wafer 44. For example, as described above, normal incidence illumination may not be as suitable as oblique incidence illumination for detection of defects on the edge of the wafer. However, light 48 may be directed to an upper and/or bottom surface of a wafer during inspection of these surfaces. The illumination subsystem may include a number of optical components (not shown) positioned in the path of light 48. These optical components may include any of those described above.

Light sources 42 and 46 may include any suitable light sources known in the art such as lasers. In a different embodiment, the system may include a single light source that is used to provide light for oblique and normal illumination. For example, a single light source such as a multi-wavelength laser may be coupled to a beam splitter, which is configured to split the light from the laser into separate beams having different wavelengths, one of which is used for normal illumination and the other of which is used for oblique illumination. The illumination subsystem may include any other suitable combination of a single light source and beam multiplier(s) known in the art. In any of the above embodiments, light 40 may have one or more characteristics such as wavelength and/or polarization that are different than the characteristics of light 48. Alternatively, light 40 may have substantially the same characteristics as light 48.

Wafer 44 is supported on a chuck (not shown) or "stage," which may be rotated and translated such that light 40 and optionally light 48 illuminates an area or spot on the wafer that moves in a spiral path. Alternatively, light 40 and 48 may be scanned over the wafer in any manner known to those skilled in the art to trace the spiral path or another type of scan path across the wafer. Since the system shown in FIG. 3 was previously used to inspect only the upper and bottom surfaces of a wafer, beams 40 and 48 were only scanned within the central region of the wafer shown in FIG. 1.

However, in one embodiment, the system shown in FIG. 3 can be modified such that at least beam 40 is scanned over the edge of the wafer. For example, scanning control software (not shown), which can be implemented using processor 50, which is described in further detail herein, can be modified such that the scan of the wafer proceeds past the nominal wafer edge. In one embodiment, the system is configured to scan the light across the edge of the specimen by scanning the light beyond a nominal edge of the specimen by a distance of about 2 mm to about 3 mm. In addition, the system may be configured to scan the light across the edge of the specimen by scanning the light from a position on an upper surface of the specimen proximate the edge to a position beyond the nominal edge of the specimen. In this manner, scanning of the wafer for edge inspection may not start at the center of the wafer as currently performed for upper surface inspection. Instead, the scan may start just inside the radius of the edge region and proceed from there past the nominal edge of the wafer to optimize throughput of the edge inspection process.

The system may also be configured to scan the light across the edge of the specimen by rotating and translating the specimen substantially simultaneously. Therefore, the propagation direction of the oblique beam is towards the wafer edge while at the same time, the rotating wafer is also translated away in the direction of propagation as well. Thus, the edge region and the entire wafer edge including the top bevel, the apex, and optionally the bottom bevel is "painted" with the oblique incidence light.

As described above, illumination of the wafer will cause scattering of the light from the wafer. In addition, both oblique incidence light and normal incidence light may be scattered from the wafer. The system shown in FIG. 3 includes a detection subsystem that is configured to collect light scattered from the specimen and to generate signals responsive to the scattered light. The signals can be used to detect defects on the specimen as described further herein.

The detection subsystem includes lens collector 52, mirror 54, beam splitter 56, and detectors 58 and 60, which form a "narrow" channel of the detection subsystem. In other words, light scattered by the illuminated area on the wafer along directions relatively close to normal to the surface of the wafer is collected and focused by lens collector 52. In this manner, lens collector 52 collects light scattered from the wafer at relatively "narrow" scattering angles. Lens collector 52 directs the collected light to mirror 54, which directs the light to beam splitter 56. Beam splitter 56 is configured to direct one portion of the light to detector 58 and the other portion of the light to detector 60. One detector may be used to detect light scattered at relatively narrow angles due to illumination by the normal incidence beam, and the other detector may be used to detect light scattered at relatively narrow angles due to the illumination by the oblique incidence beam. Detectors 58 and 60 may include any suitable detectors known in the art (e.g., photomultiplier tubes (PMTs)). In addition, detectors 58 and 60 may be similarly or differently configured. The narrow channel portion of the detection subsystem may include any other optical components (not shown) known in the art. For example, one or more polarizing components may be placed in the path of the collected light. In addition, a spatial filter may be included in the narrow channel portion of the detection subsystem to prevent the specular reflection of the normal incidence beam from reaching detectors 58 and 60.

The detection subsystem also includes ellipsoidal mirror 62, beam splitter 64, and detectors 66 and 68, which form a "wide channel" of the detection subsystem. In other words, light scattered by the illuminated area on the wafer along directions relatively far from normal to the surface of the wafer is collected and focused by ellipsoidal mirror 62. In this manner, ellipsoidal mirror 62 collects light scattered from the wafer at relatively "wide" scattering angles. Ellipsoidal mirror 62 directs the collected light to beam splitter 64. Beam splitter 64 is configured to direct one portion of the light to detector 66 and the other portion of the light to detector 68. One detector may be used to detect light scattered at relatively wide angles due to illumination by the normal incidence beam, and the other detector may be used to detect light scattered at relatively wide angles due to the illumination by the oblique incidence beam. Detectors 66 and 68 may include any suitable detectors known in the art (e.g., PMTs). In addition, detectors 66 and 68 may be similarly or differently configured. The wide channel portion of the detection subsystem may include any other optical components (not shown) known in the art. For example, one or more polarizing components may be placed in the path of the collected light.

Detectors 58, 60, 66, and 68 are configured to generate signals responsive to the scattered light. Processor 50 is coupled to detectors 58, 60, 66, and 68 by transmission media as shown by the dotted lines in FIG. 3. The transmission media may include any suitable transmission media known in the art. In addition, one or more additional components (not shown) may be interposed between the detectors and the processor such as analog-to-digital converters. In this manner, signals generated by the detectors can be sent to the processor. The processor may be configured to use the signals to detect defects on the wafer. The processor may be configured to use any algorithm or method for detecting the defects using the signals.

In most systems that are used to inspect the upper surface of a wafer, signals corresponding to light scattered from the edge of the wafer are eliminated as noise such that these signals do not interfere with the inspection. In contrast, the processor shown in FIG. 3 may be configured to use the signals responsive to light scattered from the edge of the wafer to detect defects on the edge of the wafer. The defects that may be detected as described herein include, but are not limited to, cracks, chips, particles, and delaminated film layers. In addition, defects that can be detected on the edge of a wafer using a system as described herein include defects having a size of about 5 micron to about 10 micron. Such edge defect sensitivity may be suitable particularly since most edge defects of interest such as those described above are relatively large in size.

The processor may also be configured to determine a position of the defects on the edge of the specimen using the signals. The position may be an azimuthal and radial position of the defects on the edge of the wafer. The azimuthal position of the edge defects may be defined as the position of the defects on the edge of the wafer with respect to some fixed point on the wafer such as a notch or any other alignment mark provided on the wafer. The radial position is defined as the position of the defects on the edge of the wafer with respect to the center of an upper or bottom surface of the wafer. The processor may use the detected position of the alignment mark and wafer center in combination with positional information generated during scanning to determine the azimuthal and radial position of the edge defects. If the system includes one or more components (not shown) that are configured to position the oblique incidence beam with respect to the surface of the wafer, the processor may also use information from the beam positioning component(s) to correct the positional information generated during scanning. In some embodiments, the position of the defects that is determined as described herein includes x and y coordinates of the position of the defects. In another embodiment, the edge of the specimen includes a top bevel, an apex, and a bottom bevel of the specimen as described above. In such an embodiment, the method may include determining if the defects are located on the top bevel, the apex, or the bottom bevel using the signals.

In some embodiments, the system may include display device 51, which may be used to display a user interface (not shown). The user interface may be configured to illustrate defects on a wafer map in a graphically distinct manner such that a user could readily distinguish the azimuthal and radial position of the edge defects. The processor may also be configured to use the signals generated by the detectors to determine one or more characteristics of the defects such as size, classification, root cause, etc. The processor may be configured to use any algorithm or method known in the art to determine the characteristics of the defects. The one or more characteristics of the edge defects that are determined by the processor may also be displayed in any manner in the above-described user interface.

As described above, oblique incidence is preferably used for inspection of the edge of the specimen since this illumination can illuminate the entire edge of the specimen. In addition, oblique incidence "stretches" the radial extent of the bevels and apex from a typical radial extent of about 0.5 mm to greater than about 2 mm. In other words, the oblique beam of illumination will move across the wafer slower than the normal incidence beam will. In this manner, a particular location on the edge of the wafer can be scanned over a longer period of time with the oblique incidence beam compared to the length of time that the normal incidence beam will scan over the same location. In some embodiments, the oblique incidence beam will scan over the particular location three times longer than the normal incidence beam. In this manner, scanning the edge of the wafer with the oblique incidence beam will allow more accurate determination of the locations of defects on the edge. For example, the stretching of the edge of the wafer by the oblique incidence beam will allow the processor or an algorithm used by the processor to determine whether a defect is located close to the nominal edge/top bevel transition or near the bottom of the apex, which may provide important information related to the severity and cause of the defects.

During edge inspection, therefore, the system is preferably configured to use signals generated by detector(s) that detect light scattered from the edge of the wafer as a result of oblique illumination. In some embodiments, detector 66 may be configured to generate signals responsive to light scattered from the specimen at relatively wide angles as a result of oblique incidence. In this manner, detector 66 may form a part of the DWO (darkfield, wide, oblique) channel of the detection subsystem. The light scattered at the relatively wide angles due to oblique incidence may be particularly sensitive to defects on the edge of the specimen. In particular, the light detected by detector 66 may be particularly sensitive to defects located on the top bevel, apex, and bottom bevel of the edge of the wafer. In this manner, signals generated by detector 66 may be used to detect defects on the edge of the specimen.

In addition, signals generated by the other detectors, which are responsive to light scattered from the specimen, may be used to detect defects on the edge of the specimen. These signals may be used in combination with signals from detector 66 to detect defects on the edge of the specimen.

The system described above is advantageously modified as described further herein for detection of defects on the edge of patterned and unpatterned wafers. In particular, one or more parameters of the system used for inspecting a surface of the specimen (e.g., an upper surface of a bottom surface) may be different than the parameter(s) used for inspecting an edge of the specimen. In one such embodiment, the polarization of the illumination used for edge inspection may be different than that used for surface inspection. For example, relatively large amounts of light may be scattered from the various features of the edge including nominal edge 16, the position at which top bevel 22 meets apex 24, the position at which apex 24 meets bottom bevel 26, and nominal edge 28, which are shown in FIG. 2.

Light scattered from these features in the edge of the wafer may produce "artifact rings" in the inspection data. For example, the artifact rings may appear as spatially separated bright lines in the data acquired during edge inspection. In one embodiment, the polarization of the illumination used during edge inspection may be selected to suppress the artifact rings in the inspection data. An appropriate polarization may be selected using any method known in the art. The polarization that results in suppression of the artifact rings may be different than a polarization of the illumination that is used for inspection of the upper and/or bottom surface of the wafer. In this manner, the polarization of the illumination may be changed between different inspections performed by the system.

In another embodiment, the detection subsystem may include one or more polarizing components (not shown). The polarizing components may be configured to block scattered light having a particular polarization. In particular, the features of the edge described above may alter the polarization of the incident light in a predictable manner. In addition, the polarization of this scattered light may be different than that of the light scattered from other portions of the edge of the wafer. In this manner, the polarizing components may be configured to selectively block light scattered from the features of the edge from reaching the detectors. The one or more polarizing components may be located in any suitable position in the detection subsystem. In addition, the polarizing components may be located in the optical path of the light scattered from the wafer during edge inspection, and the polarizing components may be moved out of the scattered light optical path during surface inspection. The position of the polarizing components may be altered between different types of inspections using any suitable components (not shown) known in the art.

In another embodiment, processor 50 shown in FIG. 3 may be configured to analyze the signals responsive to light scattered from the edge of the wafer using polarization characteristics of the light scattering. For example, light scattered from the features of the edge may have a different polarization than light scattered from other portions of the edge as described above. In addition, the features of the edge may alter the polarization of the incident light in a predictable manner. Therefore, the processor may use this information in addition to the polarization of the light scattering to determine which signals correspond to the artifact rings in the inspection data. The processor may then remove these signals from the inspection data, which can then be used for other purposes described herein such as edge defect detection.

The edge of the wafer will also scatter and reflect light much differently than the upper and bottom surfaces of the wafer. Such differences in the scattered and reflected light may be due at least in part to the different planes in which the upper and bottom surfaces and surfaces of the bevels and apex of the edge are located. In particular, light may be specularly reflected from the edge of the wafer at substantially different directions than light specularly reflected from the upper and bottom surfaces of the wafer. If the specularly reflected light is allowed to reach the detectors, the specularly reflected light may decrease the accuracy of the defect detection since the specularly reflected light will have a much greater intensity than that of the scattered light.

In one embodiment, the system shown in FIG. 3 may be modified such that the detection subsystem includes a mask configured to substantially prevent light specularly reflected from the edge of the specimen from impinging upon a detector of the detection subsystem. For example, the detection subsystem may include a relatively narrow mask located in the path of the light scattered from the edge of the specimen to block specularly reflected light from impinging on the detector. Preventing the specularly reflected light from impinging on the detector effectively increases the size of the defect signals relative to background light scattering from the wafer edge regions.

Such a mask may be included in the path of any of the scattered light that is used for edge defect detection. For example, detector 66 may be configured to detect light scattered at relatively wide angles resulting from illumination of the wafer by the oblique incidence beam. As such, signals generated by detector 66 responsive to this scattered light may be advantageously used for edge defect detection. In one such embodiment, mask 74 may be placed in the optical path of the light detected by detector 66, as shown in FIG. 3, during edge inspection. When inspection of the upper surface or bottom surface of the specimen is being performed by the system, mask 74 may be moved out of the optical path of the light detected by detector 66 in the direction shown by arrow 76. The mask may be moved into and out of the optical path using any appropriate components (not shown) known in the art. In addition, mask 74 may be located at any appropriate position in the optical path of the light scattered from the wafer at relatively wide angles.

Figure 4:
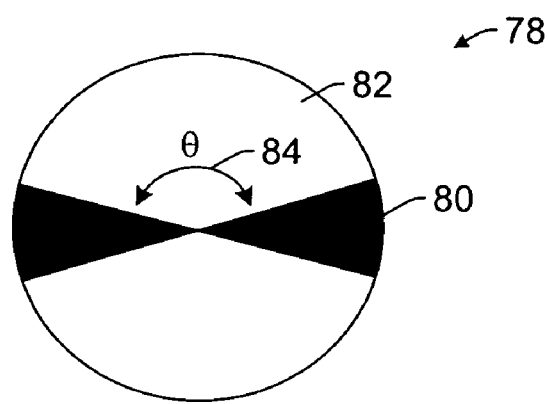
FIG. 4 is a schematic diagram illustrating a cross-sectional view of one embodiment of a mask that is configured to substantially prevent light specularly reflected from an edge of a specimen from impinging upon a detector of a detection subsystem.

One embodiment of a mask that may be included in one or more channels of the detection subsystem during edge inspection is illustrated in FIG. 4. In particular, FIG. 4 illustrates a cross-sectional view of mask 78. Mask 78 includes regions 80 that are configured to block light specularly reflected from the edge of the wafer. In addition, mask 78 includes regions 82 that are configured to transmit light scattered from the edge of the wafer. Angle 84 between edges of regions 80 defines the mask opening. The mask opening determines how much light is transmitted through the mask and eventually onto the detector. Therefore, angle 84 may be selected such that the mask can transmit as much of the scattered light as possible while blocking substantially all of the light specularly reflected from the edge of the wafer. As such, an appropriate value for angle 84 may vary depending on the characteristics of the edge of the specimen. Some examples of values of angle 84 that may be appropriate for edge inspection applications include, but are not limited to, 150°, 40°, and 20°. Although one particular type of mask is shown in FIG. 4, it is to be understood that any suitable type and configuration of mask may be used to block light specularly reflected from the edge of the wafer while transmitting light scattered from the edge of the wafer as described herein.

As described above, therefore, the system may be configured to increase the defect signal-to-noise ratio of the edge inspection by selecting the illumination polarization, by selectively blocking a portion of the scattered light based on polarization, by analyzing the polarization of the scattered light, or by using a mask to block light specularly reflected from the edge of the wafer. In addition, the system may be configured to use only one of these techniques or more than one of these techniques in any combination thereof to improve the signal-to-noise ratio. If the system is configured to use more than one of these techniques to improve the signal-to-noise ratio, each of the techniques may be used alone or in some combination thereof depending on the characteristics of the specimen being inspected.

The system shown in FIG. 3, therefore, is configured to inspect an edge of a specimen as well as to inspect an upper surface of the specimen. In addition, as described above, parameters of the system that are suitable or even advantageous for edge inspection may not be suitable at all for upper surface inspection. In one embodiment, therefore, parameters of the system that are used for inspection of the upper surface of the specimen are different than parameters of the system used for edge inspection. In this manner, if both an upper surface and edge inspection are to be performed on a wafer, one of the inspections may be performed, then the parameters of the system may be altered for the other inspection. The other inspection may then be performed. As such, multiple types of inspections may be performed on a wafer in a single inspection process that includes a parameter adjustment step between scanning/data acquisition steps.

The parameters of the system may be altered by processor 50 in some embodiments. For example, processor 50 may be coupled to one or more components of the system such as the masks and polarizing components described above. The processor may also alter one or more parameters of the component(s) based on the type of inspection that is being performed. In addition, the processor may be configured to provide a user interface that can be used to create, alter, and save different system parameters for scanning wafer centers and edges, and for sequencing a succession of wafers from a given input cassette through a normal surface scan, an edge scan, or both. The scanning parameters and sequencing may be stored in a "recipe" or a set of program instructions that may be executable by the processor for controlling the system to perform the inspection(s) with the selected parameters.

In some embodiments, the system shown in FIG. 3 may also be configured to inspect a bottom surface of the specimen. In some cases, the parameters of the system that are used for inspection of the bottom surface may be substantially the same as those used for inspection of the upper surface of the specimen. However, in most cases, the parameters used for inspection of the edge of the wafer may be different than the parameters used for bottom surface inspection. As such, an inspection process that includes edge and bottom surface inspection may be performed as described above.

In one embodiment, the system shown in FIG. 3 may be configured to inspect an edge, an upper surface, and a bottom surface of a wafer. In one such embodiment, the system may include a mechanical device that is configured to change the position of the wafer depending on whether the upper surface or the bottom surface of the wafer is being inspected by the system. For example, such an embodiment of the system may include the specimen handler shown in FIGS. 5 and 6.

Figure 5:
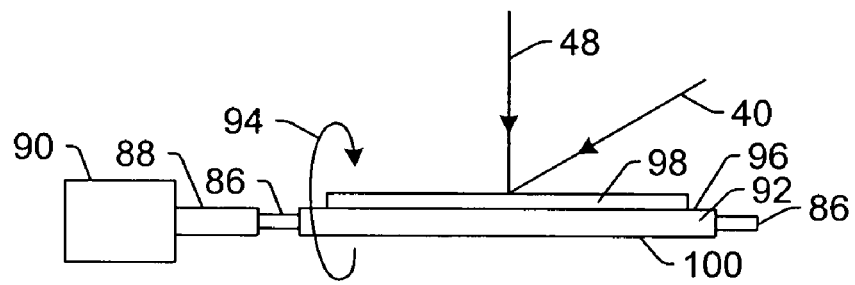
FIGS. 5-6 are schematic diagrams illustrating one embodiment of a specimen handler that may be included in a system configured to inspect an edge of a specimen.

This specimen handler includes specimen edge handler 86, which is configured to contact the edge of the specimen without contacting the upper or bottom surface of the specimen such that a position of the specimen within edge handler 86 is relatively stable. Specimen edge handler 86 is coupled to shaft 88. Shaft 88 may be coupled to rotating mechanism 90. Rotating mechanism 90 may include a motor or any other device, which in of itself may not rotate, but causes rotation of shaft 88. Rotation of shaft 88, in turn, causes rotation of specimen edge handler 86 thereby rotating specimen 92, one possible direction of which is shown by arrow 94. In this manner, when upper surface 96 of wafer 92 (on which structure 98 may be formed) is being inspected by the system, the wafer is positioned as shown in FIG. 5 such that oblique incidence beam 40 and normal incidence beam 48 of the system described above may be incident on the upper surface of structure 98.

Figure 6:
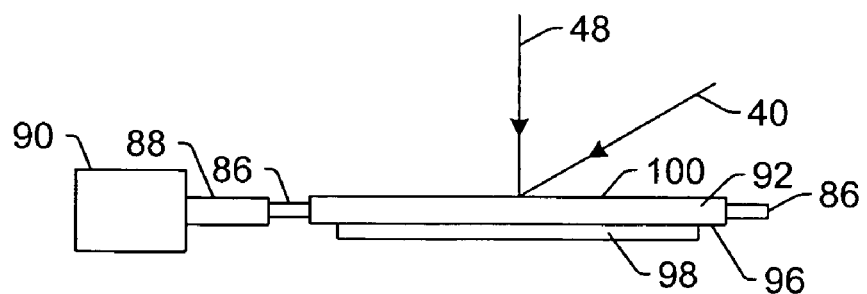

In contrast, when bottom surface 100 of wafer is to be inspected by the system, the position of the wafer may be "flipped" such that, as shown in FIG. 6, oblique incidence beam 40 and normal incidence beam 48 of the system shown in FIG. 3 are incident on the bottom surface of the wafer. As shown in FIG. 6, during inspection of the bottom surface of the wafer, edge handler 86 supports the wafer without contacting the upper surface of the wafer thereby preventing damage to the upper surface of the wafer.

In another embodiment, the system shown in FIG. 3 may include a Back Side Inspection Module (BSIM), which is commercially available from KLA-Tencor, as part of the SP1 laser-based wafer inspection tool. The BSIM enables non-destructive front side and back side inspection of a wafer through wafer edge handling and a "flipping" mechanism. Therefore, the wafer handling is designed such that the front side of the wafer is not damaged during inspection of the back side of the wafer. In this manner, back side inspection of both product and non-product wafers may be performed by the system shown in FIG. 3.

The system illustrated in FIG. 3 may be used, therefore, to inspect an entire upper surface, an entire bottom surface, and an entire edge of a wafer. In addition, the system may be used to inspect the entire upper surface, the entire bottom surface, and the edge of the wafer in a single inspection process.

As described above, the specimens that can be inspected by the systems and methods described herein include a patterned or unpatterned wafer. In this manner, the system may be used to inspect the edges of both patterned and unpatterned wafers. In some embodiments, patterned features are located on an upper surface of the specimen proximate to the edge of the specimen. For example, these patterned features may include partial chip sites present in the near-edge region. Therefore, these patterned features may affect the signals that are generated during inspection of the edge of the specimen. In one such embodiment, the processor described above is configured to determine which of the signals correspond to the light scattered from the patterned features. The processor may also be configured to eliminate the signals corresponding to the light scattered from the patterned features from the signals used to detect the defects. In this manner, the patterned feature signals may be eliminated after the inspection data has been acquired.

The processor may identify and eliminate the patterned feature signals using any method or algorithm known in the art. For example, the light scattered from patterned features may have one or more characteristics such as polarization and intensity that are different than characteristics of the light scattered from edge defects of interest. In this manner, the processor may use the characteristics of the scattered light signals to determine which signals correspond to the patterned features. In a different example, the processor may be configured to filter the signals using an algorithm such as a Fourier filtering algorithm that can be used to identify regular patterns in the signals that correspond to the signals from the patterned features.

In a different embodiment, optical components of the detection subsystem may be configured to eliminate light scattering corresponding to the patterned features on the wafer. Examples of such optical configurations are illustrated in U.S. Pat. No. 6,538,730 to Vaez-Iravani et al., which is incorporated by reference above. The systems described herein may be configured to eliminate light scattering from patterned features as described in this patent. In this manner, the systems described herein may be configured to eliminate signals corresponding to light scattered from patterned features during data acquisition or after data acquisition.

Although many different system embodiments are described above, it is to be understood that the edge inspection technique described herein may be implemented on any existing inspection system that can be (preferably easily) modified to direct light to an edge of a wafer as described above and to collect light scattered from the edge of the wafer as described above. In addition, obviously, the systems that are described herein may have many different optical configurations, and all such optical configurations are within the scope of the present disclosure.

One advantage of the systems described herein over other currently used inspection systems is that edge inspection capability is added to an established platform thereby saving an end-user the expense and effort of acquiring additional inspection systems, training in the use of the additional inspection systems, and training in the use of an unfamiliar user interface that most likely would be implemented on the additional inspection systems. In contrast, implementation of the techniques described herein may involve updating software installed on an existing system (e.g., for scanning control, edge defect mapping, and other functions described herein) and possibly the addition of one or more masks configured as described above. Therefore, the systems described herein can be deployed rapidly at the end-user's location and at relatively little cost. Furthermore, addition of the edge inspection capability described herein to an existing inspection system will create little or no change in the system performance for conventional surface scans and only a small impact to the overall system throughput when both conventional and edge scans are performed. Obviously, the relatively small reduction in throughput will be offset by the advantages described above in addition to the increased capability that edge inspection provides for process monitoring and yield control.

Figure 7:
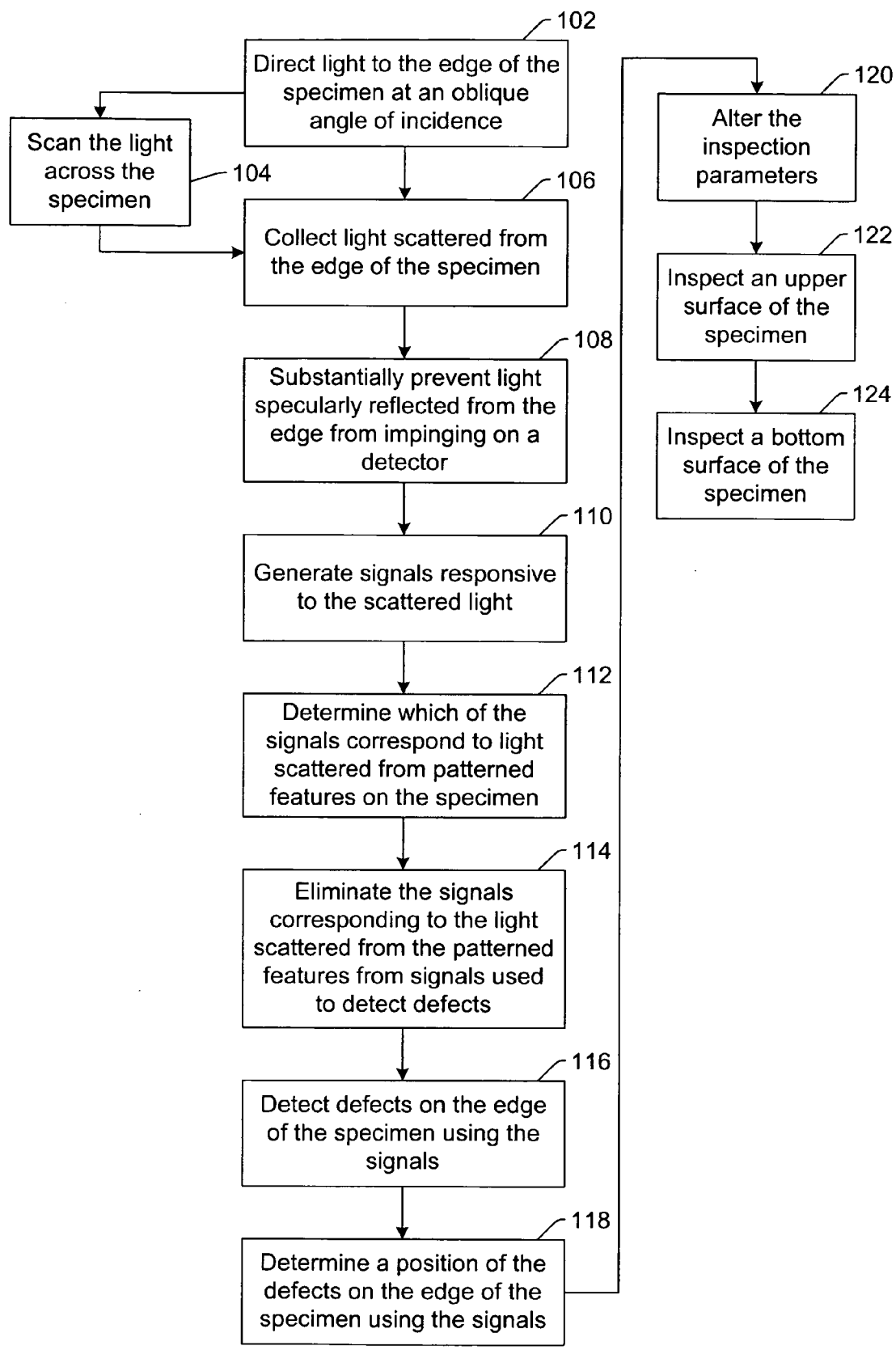
FIG. 7 is a flow chart illustrating one embodiment of a method for inspecting an edge of a specimen.

Another embodiment relates to a method for inspecting an edge of a specimen. One embodiment of such a method is illustrated in FIG. 7. Many of the steps shown in FIG. 7 are not essential to practice of the method. In particular, one or more steps may be omitted from or added to the method shown in FIG. 7, and the method can still be practiced within the scope of this embodiment. In addition, many of the steps shown in FIG. 7 do not have to be performed in the order shown in FIG. 7 unless otherwise noted herein.

The method includes directing light to the edge of the specimen at an oblique angle of incidence, as shown in step 102. The plane of incidence of the light is substantially perpendicular to a plane substantially tangent to the edge of the specimen, as described further above. The edge of the specimen may include a top bevel, an apex, and a bottom bevel, as shown in FIG. 2.

In one embodiment, directing the light to the edge of the specimen includes scanning the light across the specimen, as shown in step 104 of FIG. 7. In one such embodiment, directing the light to the edge of the specimen includes scanning the light across the edge of the specimen by rotating and translating the specimen substantially simultaneously. In another such embodiment, directing the light to the edge of the specimen includes scanning the light beyond a nominal edge of the specimen by a distance of about 2 mm to about 3 mm. In an additional embodiment, directing the light to the edge of the specimen includes scanning the light across the specimen from a position on an upper surface of the specimen proximate the edge to a position beyond a nominal edge of the specimen.

The method also includes collecting light scattered from the edge of the specimen, as shown in step 106. Collecting the light scattered from the edge of the specimen may be performed as described further above. In one embodiment, the method includes substantially preventing light specularly reflected from the edge of the specimen from impinging on a detector, as shown in step 108. The detector includes a detector that is used for generating signals responsive to the scattered light, as shown in step 110. The detector may be further configured as described above. The signals can be used to detect defects on the edge of the specimen as described further above.

The specimen may include a patterned or unpatterned wafer. The specimen may be further configured as described above. For instance, in one embodiment, patterned features may be located on an upper surface of the specimen proximate to the edge of the specimen. In one such embodiment, the method includes determining which of the signals correspond to the light scattered from the patterned features, as shown in step 112. Such an embodiment may also include eliminating the signals corresponding to the light scattered from the patterned features from the signals used to detect the defects on the edge of the specimen, as shown in step 114. Determining which of the signals correspond to the light scattered from the patterned features and eliminating the signals corresponding to the light scattered from the patterned features may be performed as described above.

As shown in step 116, the method may include detecting defects on the edge of the specimen using the signals. The defects may be detected as described further above. In some embodiments, the method includes determining a position of the defects on the edge of the specimen using the signals, as shown in step 118. Determining the position of the defects on the edge of the specimen may be performed as described herein.

Subsequent to performing the edge inspection as described above, the method may include altering the inspection parameters, as shown in step 120. In one embodiment, the method includes inspecting an upper surface of the specimen, as shown in step 122. Therefore, the inspection parameters may be altered in step 120 such that parameters used for inspecting the upper surface of the specimen are different than parameters used for inspecting the edge of the specimen. In addition, the inspection parameters may be altered as shown in step 120 any time two different portions of the specimen are inspected. For instance, as shown in step 124, the method may include inspecting a bottom surface of the specimen. In such an embodiment, the inspection parameters may be altered before the bottom surface inspection is performed if an upper surface inspection or an edge inspection was performed on the specimen before the bottom surface inspection. In this manner, the inspection used for each step of an inspection process may be optimized for the surface or edge being inspected. Each of the embodiments of the method described above may include any other step(s) described herein.

Further modifications and alternative embodiments of various aspects of the invention may be apparent to those skilled in the art in view of this description. For example, systems and methods for inspecting an edge of a specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to inspect an edge of a specimen, comprising:
    an illumination subsystem configured to direct light to the edge of the specimen at an oblique angle of incidence, wherein the plane of incidence of the light is substantially perpendicular to a plane that is substantially tangent to the edge of the specimen; and
    a detection subsystem configured to collect light scattered from the edge of the specimen and to generate signals responsive to the scattered light, wherein the signals can be used to detect defects on the edge of the specimen, wherein the system is further configured to inspect a center region of an upper surface of the specimen, wherein the center region is spaced from the edge by an edge region of the specimen, wherein an optical component of the illumination subsystem or the detection subsystem used for inspection of the edge is also used for inspection of the center region of the upper surface, wherein one or more optical parameters of the system used for inspection of the center region of the upper surface of the specimen are different than one or more optical parameters of the system used for inspection of the edge of the specimen, and wherein the detection subsystem comprises a mask configured to substantially prevent light specularly reflected from the edge of the specimen from impinging upon a detector of the detection subsystem.

2. The system of claim 1, wherein the edge of the specimen comprises a top bevel, an apex, and a bottom bevel of the specimen.

3. The system of claim 1, wherein the system is further configured to scan the light across the edge of the specimen by rotating and translating the specimen substantially simultaneously.

4. The system of claim 1, wherein the system is further configured to scan the light across the edge of the specimen by scanning the light beyond a nominal edge of the specimen by a distance of about 2 mm to about 3 mm.

5. The system of claim 1, wherein the system is further configured to scan the light across the edge of the specimen by scanning the light from a position on the upper surface of the specimen proximate the edge to a position beyond a nominal edge of the specimen.

6. The system of claim 1, further comprising a processor configured to determine a position of the defects on the edge of the specimen using the signals.

7. The system of claim 1, wherein patterned features are located on the upper surface of the specimen proximate to the edge of the specimen, the system further comprising a processor configured to determine which of the signals correspond to the light scattered from the patterned features and to eliminate the signals corresponding to the light scattered from the patterned features from the signals used to detect the defects.

8. The system of claim 1, wherein the system is further configured to inspect a bottom surface of the specimen.

9. The system of claim 1, wherein the specimen comprises a patterned or unpatterned wafer.

10. A method for inspecting an edge of a specimen, comprising:
   directing light to the edge of the specimen at an oblique angle of incidence, wherein the plane of incidence of the light is substantially perpendicular to a plane substantially tangent to the edge of the specimen;
   collecting light scattered from the edge of the specimen;
   generating signals responsive to the scattered light, wherein the signals can be used to detect defects on the edge of the specimen;
   using mask for substantially preventing light specularly reflected from the edge of the specimen from impinging upon a detector used for said generating; and
   inspecting a center region of an upper surface of the specimen, wherein the center region is spaced from the edge by an edge region of the specimen, wherein an optical component used for inspection of the edge is also used for inspection of the center region of the upper surface, and wherein one or more optical parameters used for inspecting the center region of the upper surface of the specimen are different than one or more optical parameters used for inspecting the edge of the specimen.

11. The method of claim 10, wherein the edge of the specimen comprises a top bevel, an apex, and a bottom bevel of the specimen.

12. The method of claim 10, wherein said directing comprises scanning the light across the edge of the specimen by rotating and translating the specimen substantially simultaneously.

13. The method of claim 10, wherein said directing comprises scanning the light beyond a nominal edge of the specimen by a distance of about 2 mm to about 3 mm.

14. The method of claim 10, wherein said directing comprises scanning the light across the specimen from a position on the upper surface of the specimen proximate the edge to a position beyond a nominal edge of the specimen.

15. The method of claim 10, further comprising determining a position of the defects on the edge of the specimen using the signals.

16. The method of claim 10, further comprising determining a position of the defects on the edge of the specimen using the signals, wherein the position comprises x and y coordinates of the position of the defects.

17. The method of claim 10, wherein the edge of the specimen comprises a top bevel, an apex, and a bottom bevel of the specimen, and wherein the method further comprises determining if the defects are located on the top bevel, the apex, or the bottom bevel using the signals.

18. The method of claim 10, wherein patterned features are located on the upper surface of the specimen proximate to the edge of the specimen, the method further comprising determining which of the signals correspond to the light scattered from the patterned features and eliminating the signals corresponding to the light scattered from the patterned features from the signals used to detect the defects.

19. The method of claim 10, further comprising inspecting a bottom surface of the specimen.

20. The method of claim 10, wherein the specimen comprises a patterned or unpatterned wafer.

* * * * *